US00PP37404P2

(12) United States Plant Patent
Rodriguez et al.

(10) Patent No.: US PP37,404 P2
(45) Date of Patent: May 5, 2026

(54) RASPBERRY PLANT NAMED 'DrisRaspTwentySix'

(50) Latin Name: ***Rubus idaeus* L.**
Varietal Denomination: DrisRaspTwentySix

(71) Applicant: Driscoll's, Inc., Watsonville, CA (US)

(72) Inventors: Luis Miguel Rodriguez, Ciudad Guzman (MX); Mitzi Sarai Gonzalez Castañeda, Ciudad Guzman (MX); Stephanie Castro, Ventura, CA (US); Kyle Rak, Salinas, CA (US); Matthias D. Vitten, Aptos, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 19/330,439

(22) Filed: Sep. 16, 2025

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 5/0887
See application file for complete search history.

(56) References Cited

U.S. PATENT DOCUMENTS

| | | | |
|---|---|---|---|
| PP8,022 | P | 11/1992 | Wilhelm |
| PP8,027 | P | 11/1992 | Wilhelm |
| PP9,340 | P | 10/1995 | Wilhelm et al. |
| PP9,653 | P | 10/1996 | Wilhelm et al. |
| PP9,696 | P | 11/1996 | Fear |
| PP11,067 | P | 9/1999 | Fear et al. |
| PP11,087 | P | 10/1999 | Fear et al. |
| PP11,094 | P | 10/1999 | Fear et al. |
| PP11,102 | P | 10/1999 | Fear et al. |
| PP14,761 | P2 | 5/2004 | Fear et al. |
| PP14,781 | P2 | 5/2004 | Fear et al. |
| PP14,804 | P2 | 5/2004 | Fear et al. |
| PP14,860 | P2 | 6/2004 | Fear et al. |
| PP14,903 | P2 | 6/2004 | Fear et al. |
| PP14,904 | P2 | 6/2004 | Fear et al. |
| PP18,658 | P3 | 3/2008 | Fear et al. |
| PP18,659 | P3 | 3/2008 | Fear et al. |
| PP19,137 | P3 | 8/2008 | Harrison et al. |
| PP19,656 | P2 | 1/2009 | Hamilton et al. |
| PP22,246 | P3 | 11/2011 | Hamilton et al. |
| PP22,731 | P2 | 5/2012 | Fear et al. |
| PP23,477 | P3 | 3/2013 | Hamilton et al. |
| PP24,610 | P3 | 7/2014 | Hamilton et al. |
| PP25,044 | P3 | 11/2014 | Hamilton et al. |
| PP25,045 | P3 | 11/2014 | Hamilton et al. |
| PP27,644 | P3 | 2/2017 | Hamilton et al. |
| PP28,775 | P2 | 12/2017 | Hamilton et al. |
| PP28,856 | P3 | 1/2018 | Hamilton et al. |
| PP29,402 | P2 | 6/2018 | Vitten et al. |
| PP30,577 | P2 | 6/2019 | Vitten et al. |
| PP30,733 | P2 | 7/2019 | Hamilton et al. |
| PP31,850 | P2 | 6/2020 | Hamilton et al. |
| PP32,496 | P2 | 11/2020 | Vitten et al. |
| PP32,722 | P2 | 1/2021 | Vitten et al. |
| PP33,723 | P2 | 12/2021 | Vitten et al. |
| PP33,736 | P2 | 12/2021 | Vitten et al. |
| PP33,758 | P2 | 12/2021 | Vitten et al. |
| PP34,070 | P2 | 3/2022 | Vitten et al. |
| PP35,578 | P2 | 1/2024 | Hamilton et al. |
| PP35,903 | P2 | 7/2024 | Vitten et al. |

*Primary Examiner* — Kent L Bell
(74) *Attorney, Agent, or Firm* — Morrison & Foerster LLP

(57) ABSTRACT

A new and distinct variety of raspberry plant named 'DrisRaspTwentySix', particularly selected for its fruit quality, yield, flavor, and shelf life, as well as its plant vigor and growth characteristics, is disclosed.

4 Drawing Sheets

Latin name:
Botanical classification: *Rubus idaeus* L.
Varietal denomination: The varietal denomination of the claimed variety of raspberry plant is 'DrisRaspTwentySix'.

BACKGROUND OF THE INVENTION

Raspberries are the edible fruit of a multitude of plant species in the genus *Rubus* of the rose family. Most raspberry species are in the subgenus *Idaeobatus*. Raspberry plants are perennial plants with woody stems. Many of the most important modern commercial red raspberry cultivars derive from hybrids between *R. idaeus* and *R. strigosus*. Recent breeding has resulted in cultivars that are thornless and more strongly upright, not needing staking.

Both the red and the black raspberry species have albino-like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warm climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purées, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

In order to meet these needs, the present invention is directed to an improved variety of raspberry plant. In particular, the invention relates to a new and distinct variety of raspberry plant (*Rubus idaeus* L.), which has been denominated as 'DrisRaspTwentySix'.

Raspberry plant variety 'DrisRaspTwentySix' was selected in Ciudad Guzmán, Jalisco, Mexico in March of 2019 and originated from a cross between the proprietary female parent 'RH813.2' (unpatented) and the proprietary male parent 'RJ0721.1' (unpatented). The original seedling of the new variety was first asexually propagated in Ciudad Guzmán, Jalisco, Mexico via root cuttings in May 2019.

'DrisRaspTwentySix' was subsequently asexually propagated via root cuttings, and has undergone testing in Ciudad Guzmán, Jalisco, Mexico for four years (2020 to 2024). The present variety has been found to be stable and reproduce true to type through successive asexual propagations via root cuttings and tissue culture.

'DrisRaspTwentySix' was particularly selected for its fruit quality, yield, flavor, and shelf life, as well as its plant vigor and growth characteristics.

BRIEF DESCRIPTION OF THE DRAWINGS

This new raspberry plant is illustrated by the accompanying photographs. The colors shown are as true as can be reasonably obtained by conventional photographic procedures. The photographs are of plants that are one year old 'DrisRaspTwentySix' has a Breeder reference code known as 'RQ4033.4'.

DETAILED BOTANICAL DESCRIPTION

Figure 1:
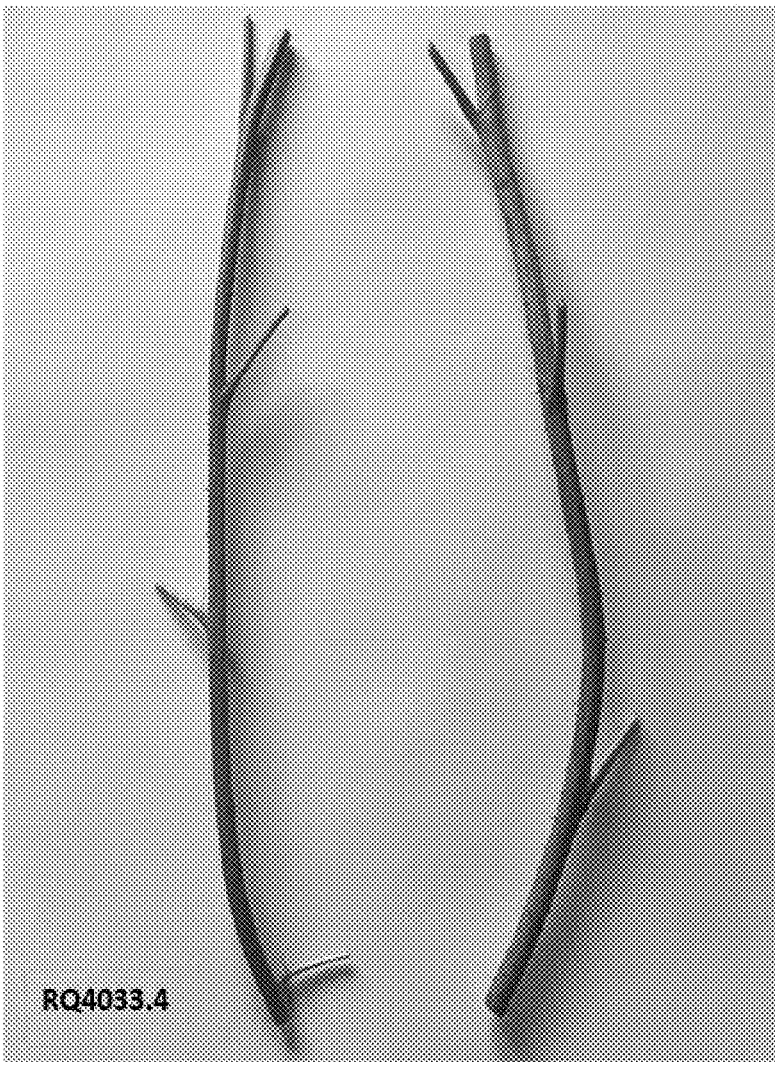
FIG. 1 illustrates sections of canes of raspberry variety 'DrisRaspTwentySix'.
Figure 2:
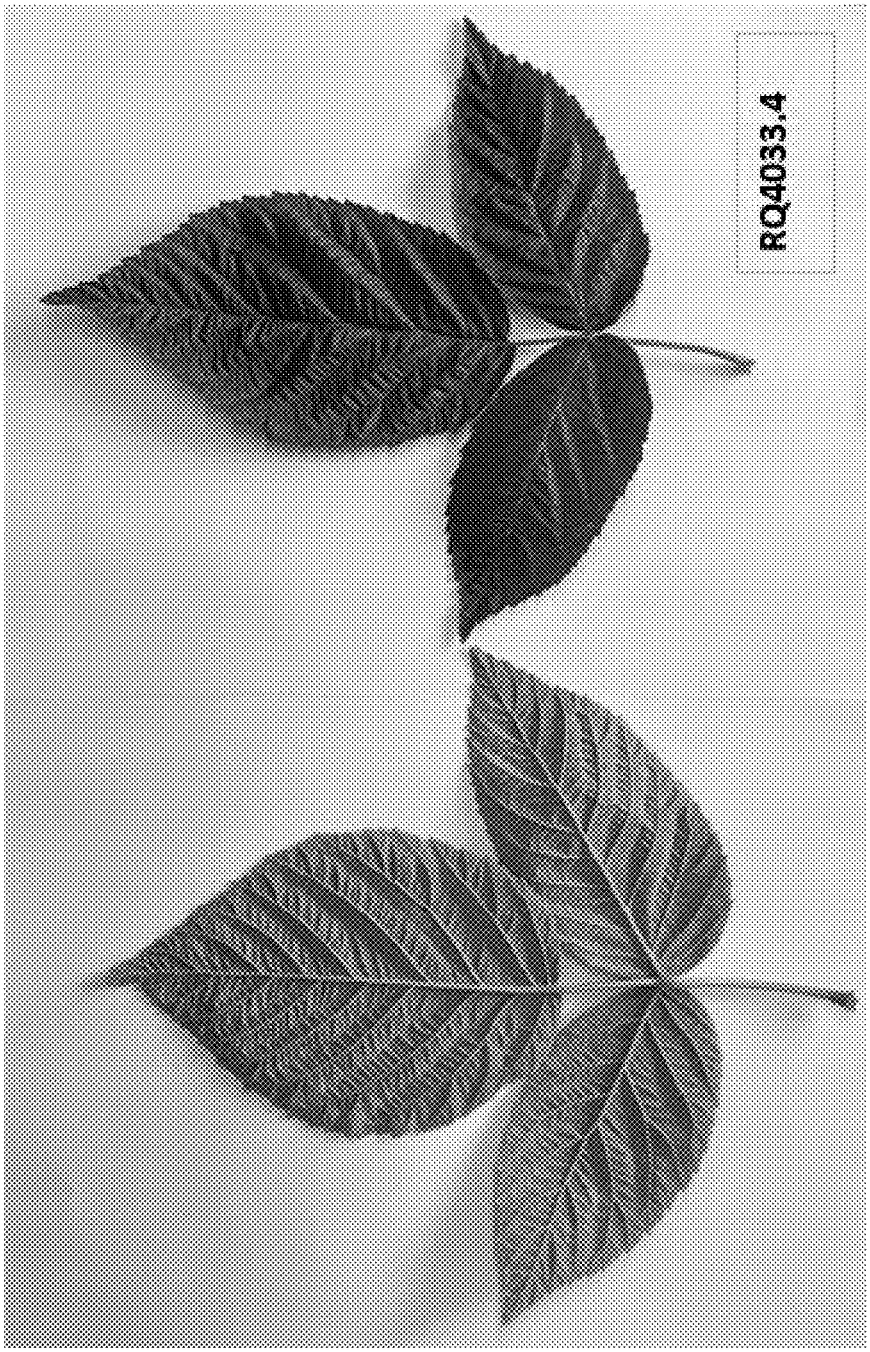
FIG. 2 illustrates the lower (left) and upper (right) surface of leaves of raspberry variety 'DrisRaspTwentySix'.
Figure 3:
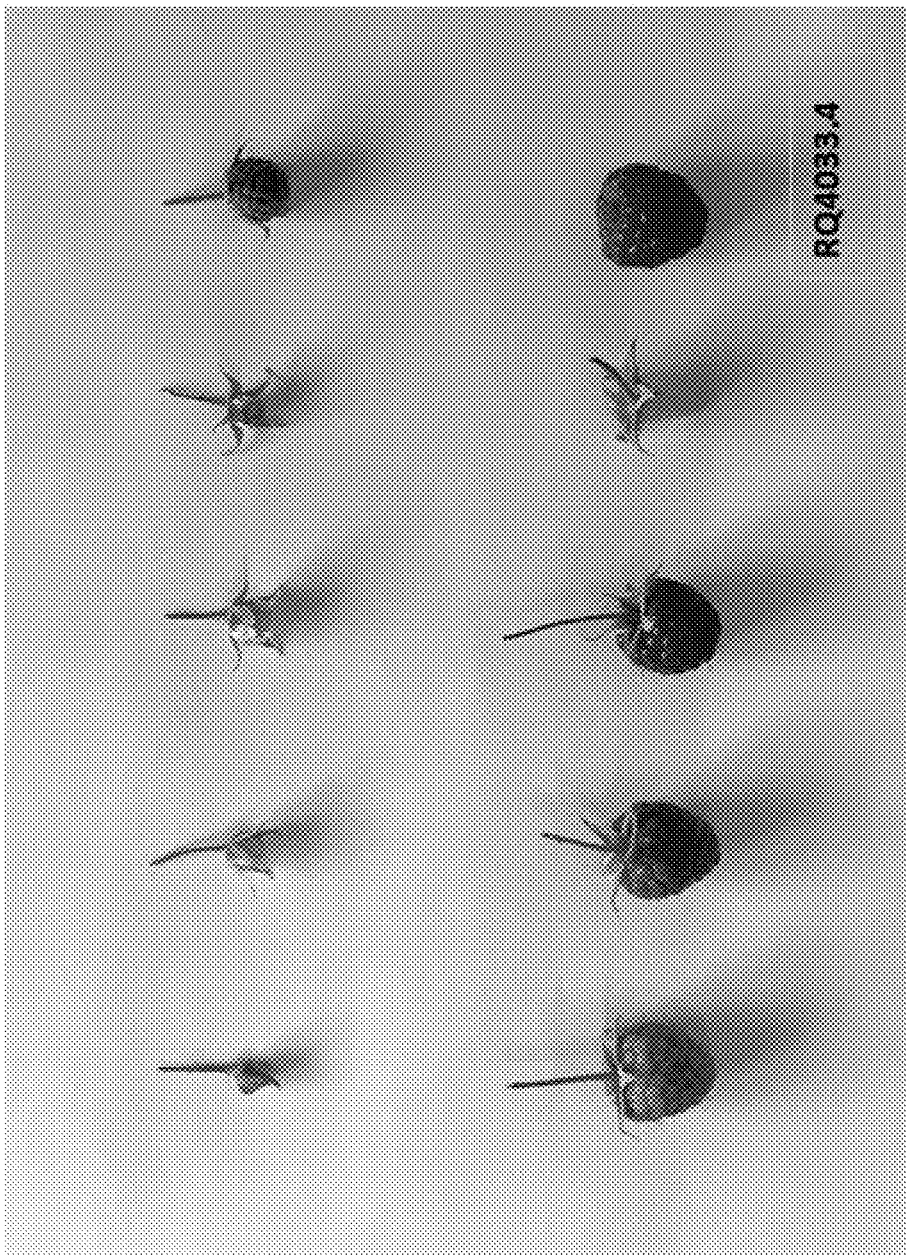
FIG. 3 illustrates flowers and fruit of raspberry variety 'DrisRaspTwentySix' at various stages of development.
Figure 4:
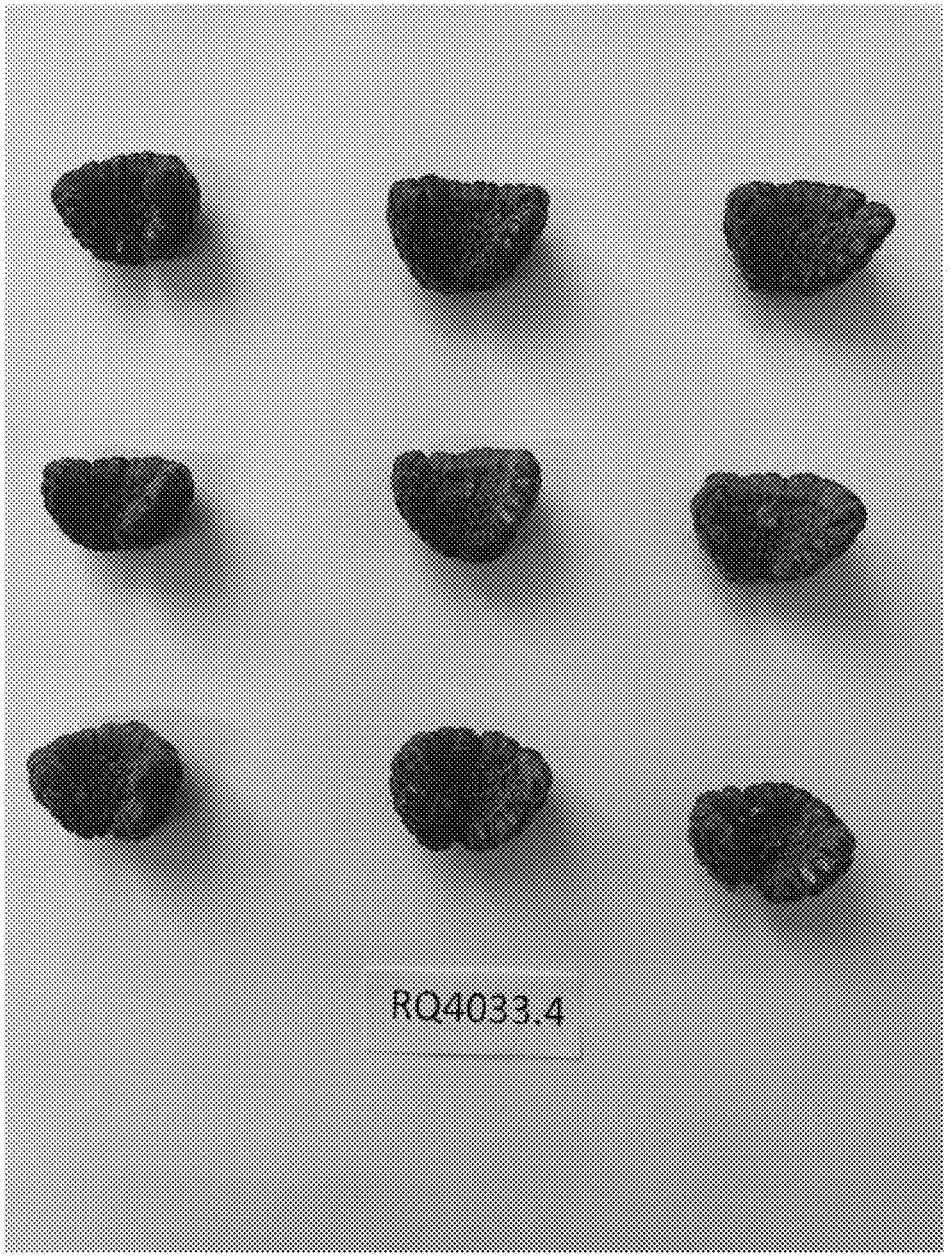
FIG. 4 illustrates the interior view of longitudinal sections of mature fruit of raspberry variety 'DrisRaspTwentySix' removed from the torus.

The following descriptions set forth the distinctive characteristics of 'DrisRaspTwentySix'. Unless where otherwise noted, the data that define these characteristics are based on observations taken from 'DrisRaspTwentySix' plants that were one year old, grown in Ciudad Guzmán, Jalisco, Mexico from 2020 to 2024. These descriptions are in accordance with UPOV terminology. Color designations, color descriptions, and other phenotypical descriptions may deviate from the stated values and descriptions depending upon variation in environmental, seasonal, climatic and cultural conditions. 'DrisRaspTwentySix' has not been observed under all possible environmental conditions. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Rosaceae.

*Botanical*.—*Rubus idaeus* L.

*Common name*.—Raspberry.

*Variety name*.—'DrisRaspTwentySix'.

Parentage:

*Female parent*.—'RH813.2' (unpatented).

*Male parent*.—'RJ0721.1' (unpatented).

Plant:

*Height*.—204.5 cm.

*Width*.—59.0 cm.

*Length/width ratio*.—3.5.

*Growth habit*.—Semi-upright.

*Self-fruitness*.—Self-fruitful.

*Time of vegetative bud burst*.—Late August.

*Time of cane emergence*.—Early June.

*Primocane* (*current year's cane*).—Cane length: 161.6 cm. Cane diameter: 1.169 cm. Internodal distance at central ⅓ of cane: 7.81 cm. Vegetative bud length at central ⅓ of cane: 4.55 mm. Anthocyanin coloration of cane: Absent. Cane color: RHS 144A (Strong yellow green). Cane bloom: Absent. Shape of cane in cross-section: Rounded. Pubescence: Absent.

*Very young shoot*.—Anthocyanin coloration of apex during rapid growth: Absent.

*Floricane* (*previous year's cane*).—Cane length: 202.6 cm. Cane diameter: 1.48 cm. Dormant cane color: About RHS 166A to 166D (Moderate reddish brown). Fruiting lateral attitude: Semi-upright. Fruiting lateral length: 40 cm.

*Prickles* (*spines*).—Presence: Present. Diameter (at base): 0.47 mm. Length (from base to tip): 1.7 mm. Color: RHS 178A (Greenish red). Attitude of tip: Downward. Presence and distribution on petioles: Present.

Leaves:

*Predominant number of leaflets*.—Three.

*Color of upper side*.—About RHS NN137A (Greyish olive green).

*Color of lower side*.—RHS N138C (Pale green).

*Arrangement of leaflets*.—Free.

*Arrangement*.—Alternate.

*Terminal leaflet*.—Length: 12.9 cm. Width: 8.6 cm. Length/width ratio: 1.5. Overall shape: Ovate. Shape of apex: Convex. Shape of base: Cuneate. Margin: Doubly serrate. Profile in cross section: Straight. Undulation: Weak.

*Lateral leaflets*.—Length: 9.4 cm. Width: 5.35 cm. Length/width ratio: 1.75. Overall shape: Ovate. Shape of apex: Convex. Shape of base: Cuneate. Margin: Doubly serrate.

*Rachis length between terminal leaflet and adjacent lateral leaflets*.—36.07 mm.

*Petiole*.—Length: 66.97 mm. Diameter: 2.31 mm. Color: RHS 145A (Strong yellow green).

*Stipule*.—Orientation: Clasping.

Flowers:

*Percent of cane flowering on primocanes*.—50%.

*Diameter*.—7.3 mm.

*Petal*.—Length: 6.27 mm. Width: 2.85 mm. Length/width ratio: 2.2. Color: RHS NN155B (White).

*Pedicel*.—Length: 26.91 mm. Diameter: 0.89 mm. Number of spines on pedicel: 33.6. Color: RHS 144C (Strong yellow green). Anthocyanin coloration: Absent.

*Peduncle*.—Length: 36.29 mm. Diameter: 1.95 mm. Color: RHS 146C (Moderate yellow green). Anthocyanin coloration: Absent.

Fruit:

*Length*.—24.85 mm.

*Diameter*.—22.33 mm.

*Length/width ratio*.—1.11.

*Weight* (*primocane*).—6.0 g/fruit.

*Weight* (*floricane*).—5.7 g/fruit.

*Sweetness/soluble solids* (° *brix*).—8.5.

*Length of single drupe*.—4.6 mm.

*Diameter of single drupe*.—4.07 mm.

*Average number of drupes per fruit*.—81.

*Shape of fruit in lateral view*.—Broad conical.

*Color*.—RHS 42B (Strong reddish orange).

*Color of torus at distal end*.—RHS 155A (Pale yellow green).

*Adherence to torus*.—Weak.

Production:

*Main bearing type*.—Both on previous year's cane in summer (floricane) and on current year's cane in autumn (primocane).

*Primocane* (*current year's cane*).—Flowering interval: Late February to early May. Fruiting period: Mid-March to June. Percent of total yield from primocane: 39% of total yield. Yield: Up to 13,231 kg of marketable fruit per hectare from the primocane crop when grown in Ciudad Guzmán, Jalisco, Mexico.

*Floricane* (*previous year's cane*).—Flowering interval: Mid-August to early November. Fruiting period: Early September to early December. Yield: Up to 15,572 kg of marketable fruit per hectare from the floricane crop from when grown in Ciudad Guzmán, Jalisco, Mexico.

COMPARISONS TO PARENTAL AND REFERENCE RASPBERRY VARIETIES

'DrisRaspTwentySix' differs from the proprietary female parent 'RH813.2' (unpatented) in that 'DrisRaspTwentySix' has improved flavor, larger fruit size, and improved shipping and storage quality as compared to 'RH813.2'.

'DrisRaspTwentySix' differs from the proprietary male parent 'RJ0721.1' (unpatented) in that 'DrisRaspTwentySix' has larger fruit size and improved shipping and storage quality as compared to 'RJ0721.1'.

'DrisRaspTwentySix' differs from reference raspberry variety 'DrisRaspThirteen' (U.S. Plant Pat. No. 29,402) in that 'DrisRaspTwentySix' has absent anthocyanin coloration of very young shoot apex during rapid growth, sparse prickle density, light red fruit color, and the predominant number of leaflets is three, whereas 'DrisRaspThirteen' has medium anthocyanin coloration of very young shoot apex during rapid growth, medium prickle density, dark red fruit color, and the predominant number of leaflets is equally three and five.

'DrisRaspTwentySix' differs from reference raspberry variety 'DrisRaspTwelve' (U.S. Plant Pat. No. 30,577) in that 'DrisRaspTwentySix' has absent anthocyanin coloration of very young shoot apex during rapid growth, medium green color of the upper leaf side, broad conical fruit shape in lateral view, and light red fruit color, whereas 'DrisRaspTwelve' has medium anthocyanin coloration of very young shoot apex during rapid growth, dark green color of the upper leaf side, trapezoidal fruit shape in lateral view, and light orange fruit color.

What is claimed is:

1. A new and distinct variety of raspberry plant designated 'DrisRaspTwentySix' as shown and described herein.

* * * * *